United States Patent [19]

Boone

[11] Patent Number: 5,047,504

[45] Date of Patent: Sep. 10, 1991

[54] METHOD FOR PURIFYING GRANULOCYTE-MACROPHAGE COLONY STIMULATING FACTOR

[75] Inventor: Thomas C. Boone, Newbury Park, Calif.

[73] Assignee: Amgen, Inc., Thousand Oaks, Calif.

[21] Appl. No.: 312,294

[22] Filed: Feb. 17, 1989

Related U.S. Application Data

[63] Continuation of Ser. No. 43,331, Apr. 28, 1987, abandoned.

[51] Int. Cl.$^5$ .................................................. C07K 3/28
[52] U.S. Cl. ..................................... 530/351; 530/395; 530/412; 530/416; 530/417; 530/418; 530/419; 530/420; 530/820; 435/69.5; 435/69.1
[58] Field of Search ........ 530/351, 395, 412, 416–420, 530/820; 435/68, 69.5, 69.1

[56] References Cited

U.S. PATENT DOCUMENTS

| | | | |
|---|---|---|---|
| 4,831,120 | 5/1989 | Ariv et al. | 530/412 |
| 4,912,200 | 3/1990 | Leibowitz | 530/351 |
| 4,923,967 | 5/1990 | Babbitt et al. | 530/351 |
| 4,929,700 | 5/1990 | Halenbeck et al. | 530/417 |
| 4,931,543 | 6/1990 | Halenbeck et al. | 530/417 |

OTHER PUBLICATIONS

Martin, *Biochem J.* 240, 1986, pp. 1–12.
Davis et al., *Nature*, 283, 1980, pp. 433–438.
Miyajima et al., *EMBO*, 5(6), 1986, pp. 1193–1197 Std.
Menge et al., *Develop. Biol. Std.*, vol. 66, 1987, pp. 391–401.
Sparrow et al., *PNAS*, 82, 1985, pp. 292–296.

*Primary Examiner*—Garnette D. Draper
*Attorney, Agent, or Firm*—Steven M. Odre

[57] ABSTRACT

A process for isolating and purifying GM-CSF produced from recombinant sources. The process provides for the isolation and purifying of recombinant GM-CSF produced in *E. coli*.

13 Claims, 1 Drawing Sheet

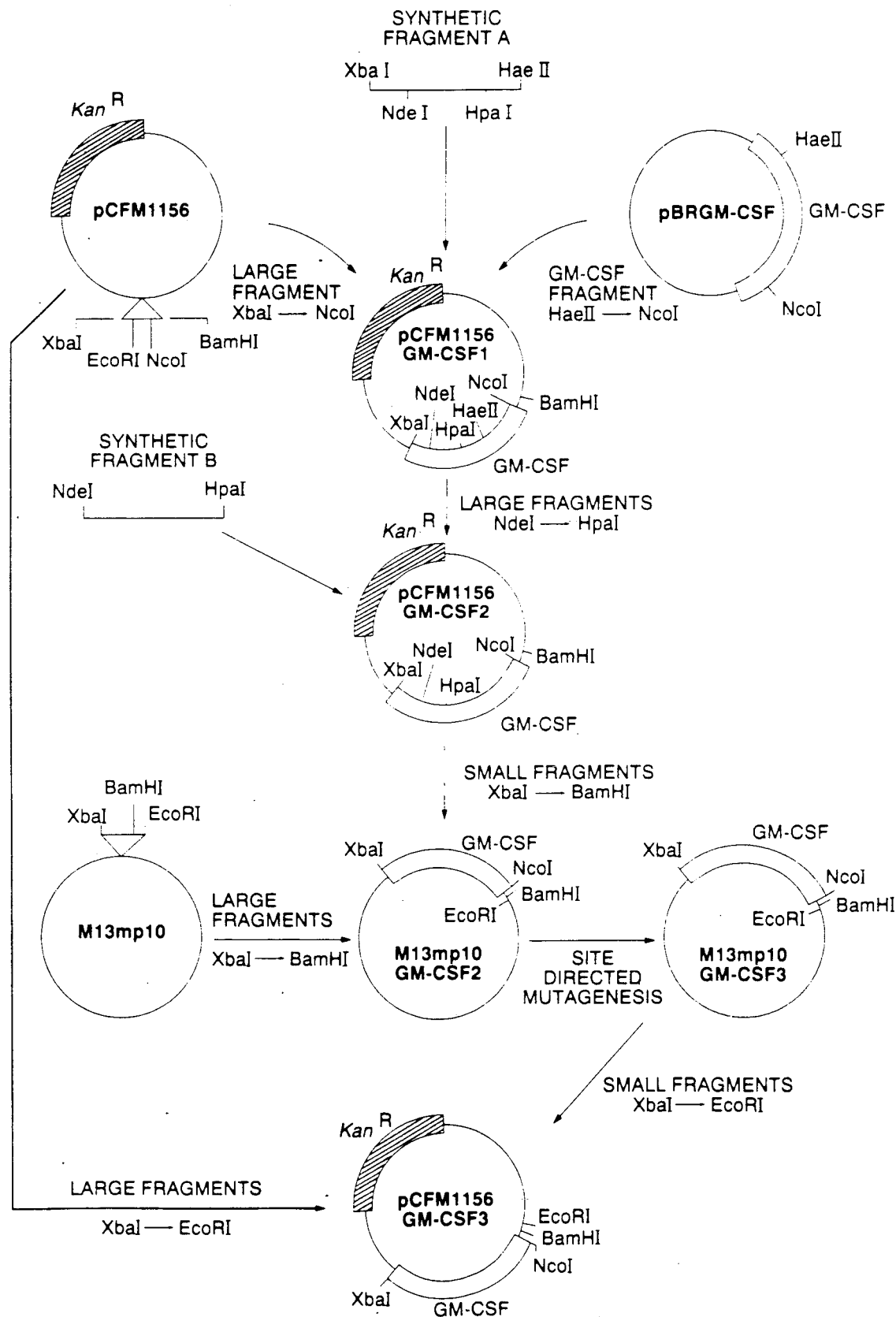

5,047,504

METHOD FOR PURIFYING GRANULOCYTE-MACROPHAGE COLONY STIMULATING FACTOR

This is a continuation of application Ser. No. 043,331, filed Apr. 28, 1987, which was abandoned upon the filling hereof.

The present invention provides a method for purifying granulocyte-macrophage colony stimulating factor ("GM-CSF") produced from recombinant sources. More particularly, the present invention relates to procedures for rapid and efficient isolation and purification of biologically active GM-CSF produced from a transformed *E. coli* microorganism.

BACKGROUND

Colony-stimulating factors are glycoproteins that stimulate the growth of hematopoietic progenitors and enhance the functional activity of mature effector cells. Human GM-CSF is a 22-kDa glycoprotein that stimulates the growth of myeloid and erythroid progenitors in vitro and increases the responsiveness of neutrophils, monocytes, and eosinophils to physiologic stimuli.

Wong et al., *Science* Vol. 228, pp. 810-815 (1985) and Kaushansky et al., *Proc. Natl. Acad. Sci. USA*, Vol. 83, pp. 3101-3105 (1986) have described the production of recombinant GM-CSF in mammalian cells. Burgess et al., *Blood*, Vol. 69, pp. 43-51 (1987) describes the purification of GM-CSF produced in *Escherichia coli*.

The extensive application of recombinant methodologies to the large scale preparation of eucaryotic proteins has substantially enhanced the prospects for obtaining desired molecules in quantity and in some instances even simplified purification procedures needed to obtain biologically active materials. Illustratively, where the desired recombinant proteins need not be glycosylated to possess biological activity, large quantities of protein can often be produced in *E. coli* recombinant hosts in the form of insoluble "inclusion bodies" which contain few proteinaceous contaminants, proteases, or the like. Host cell lysates frequently include proteinaceous constituents of sufficiently similar molecular weight, charge, polarity and solubility characteristics (vis-a-vis the recombinant protein) to make ready separation difficult. Further proteolytic enzymes endogenous to the host provide a relatively chronic source of biological activity loss for the desired protein.

In accordance with the procedure described by Burgess et al., bacterially produced GM-CSF was lysed from the microorganism, suspended in guanidinium hydrochloride and mercaptoethanol and chromatographed over G-100 Sephadex. The fractions were collected and the denaturant and reductant removed by dialysis against neutral Tris buffer. The final purification step was gradient elution from a reverse-phase support at pH 2.1.

SUMMARY OF THE INVENTION

The present invention provides a novel process for isolating and purifying GM-CSF from a GM-CSF producing microorganism comprising:

1) lysing the microorganism and separating insoluble material containing GM-CSF from soluble proteinaceous material;
2) solubilizing the GM-CSF present in the insoluble material;
3) oxidizing the GM-CSF in the presence of a reducing agent;
4) selectively separating correctly folded GM-CSF from incorrectly folded GM-CSF by precipitating the incorrectly folded GM-CSF and retaining correctly folded GM-CSF in solution;
5) recovering purified GM-CSF from the solution.

BRIEF DESCRIPTION OF THE DRAWINGS

FIG. 1 is a schematic representation of the preparation of plasmid pCFM1156 GM-CSF3.

DETAILED DESCRIPTION

As used herein the term "GM-CSF" refers to a protein that is produced by a microorganism that has been transformed with a GM-CSF gene or modification thereof that encodes a protein having (1) an amino acid sequence that is at least substantially identical to the amino acid sequence of native GM-CSF and (2) biological activity that is common to native GM-CSF. Substantial identical amino acid sequence means that the sequences are identical or differed by one or more amino acid alterations (i.e., deletions, additions, substitutions) that do not produce an adverse functional dissimilarity between the synthetic protein in native GM-CSF.

As used herein the term "GM-CSF producing microorganism" refers to a microorganism that has been genetically engineered to produce a protein that possesses biological activity associated with GM-CSF. As used herein the term "biological activity of GM-CSF" includes therapeutic activity of GM-CSF. The microorganisms are grown in a suitable growth media, the composition thereof will depend upon the particular microorganism involved. The cells are harvested from the culture, and may be concentrated if necessary, by filtration, centrifugation, and other conventional methods.

In accordance with the procedures of the present invention, the cell membranes of the microorganisms are lysed using conventional techniques such as homogenization, sonication, or pressure cycling. Preferred methods include sonication or homogenization with a Manton-Gaulin homogenizer. After the cells have been lysed, the particulate matter containing GM-CSF is separated from the liquid phase of lysate and resuspended in water. The particulate matter may be optionally washed to remove any water soluble *E. coli* proteins therein. The GM-CSF in the particulate matter is solubilized in the presence of a solubilizing agent preferably under basic pH conditions. The solubilizing agent is a chaotropic agent (i.e., a protein denaturant that dissociates hydrogen bonds and effects the tertiary structure of the proteins) generally in an aqueous solution. Representative chaotropic agents include urea and guanidinium hydrochloride. Urea is preferred. The concentration of the chaotropic agent will depend upon the particular agent that is used and the amount of cellular material present. Preferably a urea solution having a concentration of 6-8M is employed and most preferably an 8M urea solution is employed. The pH may be adjusted by adding suitable buffers, and preferably the pH will range from about 8 to about 9.0.

Following solubilization of the GM-CSF, insoluble particulate matter is separated and discarded. The soluble GM-CSF is oxidized in the presence of a reducing agent. It has been found that the yield of correctly folded GM-CSF, that is, oxidized GM-CSF having the correct native conformation of disulfide bonds, is increased by facilitating rearrangement of disulfide bonds through the use of a glutathione redox buffer (glutathione and oxidized glutathione). The GM-CSF is oxidized by the oxidized glutathione and the presence of the reducing agent, glutathione, in the redox buffer substantially reduces the formation of incorrectly folded GM-CSF, that is GM-CSF with incorrect disulfide bonds. The ratio of glutathione: oxidized glutathione in the redox buffer is readily ascertained by one of ordinary skill in the art. Preferably an excess of glutathione is employed, more preferably a ratio of from 2:1 to 10:1 on a weight basis glutathione: oxidized glutathione is employed. Most preferably a 5:1 ratio on a weight basis of glutathione: oxidized glutathione is employed.

The resulting solution is concentrated and any remaining particulate matter is removed. Preferably, the concentrated solution is buffer exchanged to remove residual urea and glutathione. The correctly folded GM-CSF is selectively separated from incorrectly folded GM-CSF by adjusting the pH of the concentrated solution to a pH range of from about 4.5 to 6.0 and preferably to 5.0 to 5.5 using an appropriate acid such as acetic acid. It has been found that within this pH range (i.e., 4.5-6.0) incorrectly folded GM-CSF is precipitated and the correctly folded GM-CSF remains soluble in solution. The resulting mixture is centrifuged and any insoluble particulate matter is removed and the soluble correctly folded GM-CSF is recovered from the remaining solution. Preferably the purified GM-CSF (i.e., correctly folded GM-CSF) is separated from any remaining contaminants employing chromatographic procedures. It is preferred to employ ion exchange or reverse phase high pressure liquid chromatography or combinations thereof to recover the purified GM-CSF. In a preferred mode of practice of this aspect of the invention, high yields of purified GM-CSF are recovered through use of a CM-Sepharose ion exchange column followed by separation using a C4 silica gel column in Tris buffer containing about 60% aqueous ethanol. Culture supernatants are preferably concentrated before chromatographic treatment and suitable steps are taken to remove ethanol from the collected eluent fraction containing GM-CSF. The ethanol may be removed using ion exchange chromatography. The GM-CSF thus separated may be formulated with pharmaceutically acceptable adjuvants, preferably phosphate buffered saline (pH 7.5) to yield a final product that is acceptable for administration to patients.

The following examples serve to further illustrate the embodiments of the present invention.

EXAMPLE 1

Expression of GM-CSF

A cDNA library constructed from the RNA obtained from bladder carcinoma cell line 5637 ((subclone 1A6) as obtained from Dr. Platzer, University of Erlangen-Nurnberg, West Germany) was probed with the oligonucleotide:

GGC-ACT-GTG-GCC-TGC-AGC-ATC-TCT-GCA-CCC-GCC-CGC to obtain positive clones for GM-CSF in accordance with the procedures of Norandler et al., Gene, Vol. 26, pp. 101–106 (1983). One of these clones herein identified as pBR GM-CSF was sequenced using the dideoxy method, and the coding sequence was the same as the sequence described by Wong et al., Science, Vol. 228, pp. 812 (1985) except for the amino acid at position 100 in the mature protein. The Wong et al. sequence had the codon ACT coding for threonine, while the sequence for the positive clone obtained herein had the codon ATT coding for isoleucine.

The GM-CSF gene was cloned for expression into an E. coli expression vector, pCFM1156, using a synthetic sequence containing a ribosome binding site, an amino terminal methionine, and the first 25 amino acids of the mature protein, along with the portion of the cDNA clone containing the carboxy terminal 102 amino acids and termination codon.

Although any suitable vector may be employed to express this DNA, the expression plasmid pCFM1156 may readily be contructed from a plasmid pCFM836, the construction of which is described in published European Patent Application No. 136,490. pCFM836 is first cut with NdeI and then blunt-ended with PolI such that both existing NdeI sites are destroyed. Next, the vector is digested with ClaI and SacII to remove an existing polylinker before ligation to a substitute polylinker as illustrated in Table I. This substitute polylinker may be constructed according to the procedure of Alton, et al., PCT Publication No. WO83/04053. Control of expression in the expression pCFM1156 plasmid is by means of a lambda $P_L$ promoter, which itself may be under the control of a $C_{1857}$ repressor gene (such as is provided in E. coli strain K12ΔHtrp).

The plasmid pCFM1156 was cut with XbaI and NcoI and the large DNA fragment was isolated. The synthetic Fragment A contained an XbaI end, a HaeII end, and internal HpaI and NdeI sites and has the following sequence:

```
        XbaI                        NdeI
    CTAGAAGGAGGAATAACATATGGCTCCGGCTCGTTCCCCGTCC
        TTCCTCCTTATTGTATACCGAGGCCGAGCAAGGGGCAGG
                                          HpaI                        HaeII
    CCGTCCACCCAGCCGTGGGAACATGTTAACGCTATCCAGGAAGCTCGGCGC
    GGCAGGTGGGTCGGCACCCTTGTACAATTGCGATAGGTCCTTCGAGC
```

TABLE 1

```
  1 ATCGATTTGATTCTAGAAGGAGGAATAACATATGGTTAACGCGTTGGAATTCGGTACCAT
    TAGCTAAACTAAGATCTTCCTCCTTATTGTATACCAATTGCGCAACCTTAAGCCATGGTA

1 ClaI, 12 XbaI, 29 NdeI, 35 HincII, HpaI, 39 MluI, 47 EcoRII, 53 HgiCI  KpnI, 57 NcoI StyI.

61 GGAAGCTTACTCGAGGATCCGCGGATAAATAAGTAACGATCC
    CCTTCGAATGAGCTCCTAGGCGCCTATTTATTCATTGCTAGG
```

TABLE 1-continued

63 HindIII, 70 AvaI XhoI, 75 BamHI Xho2, 79 Sac2.

The GM-CSF cDNA clone, pBR GM-CSF was cut HaeII to NcoI and the DNA fragment was gel purified. The three DNA fragments were ligated together to generate plasmid pCFM1156 GM-CSF1.

To increase expression of the GM-CSF, the region from NdeI to HpaI was replaced with synthetic Fragment B having the following sequence:

```
Nde1                                                        Hpa1
TATGGCACCTGCTCGTTCACCGTCACCGTCCACTCAACCGTGGGAACATGTT
    ACCGTGGACGAGCAAGTGGCAGTGGCAGGTGAGTTGGCACCCTTGTACAA
```

The plasmid pCFM1156 GM-CSF1 was cut with NdeI and HpaI and phosphatased. It was then ligated with synthetic Fragment B to generate pCFM1156 GM-CSF2.

In addition, to further increase expression of GM-CSF, the codon for leucine at position 25 was changed from CTC to CTG. This modification reduces RNA secondary structure and was accomplished by site directed mutagenesis. The GM-CSF containing region of the plasmid pCFM1156 GM-CSF2 was cloned into M13mp10 from XbaI to BamHI to generate M13mp10 GM-CSF2. Site directed mutagenesis was performed using the oligonucleotide TCGGCGCCTGCTGAACCTGA, and positive clones (M13mp10 GM-CSF3) were identified by hybridizing to this same oligonucleotide phosphorylated with $^{32}$P. The sequence was confirmed by dideoxy sequencing, and the GM-CSF containing region was cloned into pCFM1156 from XbaI to EcoRI to generate pCFM1156 GM-CSF3. The pCFM1156 GM-CSF3 was transformed into an appropriate expression vector to yield a GM-CSF producing microorganism.

EXAMPLE 2

The GM-CSF producing microorganism was inoculated under a laminar airflow hood into Fernbach flasks, each containing Luria broth (Luria Broth: Bactotryptone 10 g/L, Yeast Extract 5 g/L, NaCl 5 g/L).

The inoculated flasks were shaken at approximately 28° C. until the cell density was approximately 0.5 OD units. The flasks were then rapidly shifted to 42° C. and were maintained at 42° C. for 3 hours and a cell paste was harvested by centrifugation.

EXAMPLE 3

Cell paste containing GM-CSF in transformed *E. coli* cells, such as obtained from Example 2, was dispersed with a Brinkman homogenizer at a temperature of approximately 3° C. until completely dispersed. The suspension was passed through a Gaulin homogenizer three times. The homogenate was maintained at a temperature of less than 18° C. The homogenate was diluted to 6 parts water and the resulting mixture was centrifuged at a temperature of 3° C. The supernatant was decanted and the remaining residue was resuspended with water to yield a mixture having a final volume of 6 parts water. The resulting mixture was centrifuged at a temperature of 3° C. and the supernatant was decanted and the remaining residue was resuspended with water to yield a mixture having a final volume of 0.9 parts water. To the resulting mixture was added 0.3 parts of 1M Tris (pH 8.5) and 4.8 parts of 10M urea. The resulting mixture was centrifuged at a temperature of 14° C. and the supernatant was collected. To the supernatant was added a solution containing 0.04 parts glutathione and 0.008 parts oxidized glutathione in 54 parts of 20 mM Tris (pH 8.5). The resulting mixture was maintained at approximately 5° C. for 20 hours. The mixture was concentrated by passing through a 10,000 MW membrane. The retentate was diafiltered through a 10,000 MW membrane at 5° C. with at least 30 parts of 20 mM Tris (pH 8.5). The pH of the retentate was adjusted to pH 5.3 with 50% acetic acid. The mixture was centrifuged at a temperature of 3° C. The supernatant was removed and was loaded onto a CM-Sepharose column and eluted with 20 mM sodium acetate, 45 mM NaCl (pH 5.4). The pH of the eluent was adjusted to pH 7.7 with 1M Tris (pH 8.5). The eluent from the CM-Sepharose column was chromatographed on a C4 Silica column at 5° C. using first 20% ethanol, 50 mM Tris (pH 7.7) and then 40% ethanol, 50 mM Tris (pH 7.7). Biologically active GM-CSF was eluted from the column with a gradient from 40% ethanol, 50 mM Tris-HCl (pH 7.7) to 60% ethanol, 50 mM Tris-HCl (pH 7.7). The eluent collected was chromatographed on a DEAE-Sepharose column at 5° C. using 20 mM Tris (pH 7.7), then 10 mM NaPO$_4$ (pH 7.5) and then 10 mM NaPO$_4$, 15 mM NaCl (pH 7.5). The GM-CSF was eluted off the column with 10 mM NaPO$_4$, 60 mM NaCl, pH 7.5. The eluent containing purified GM-CSF was diluted with water to a final concentration of 0.5 mg/ml with 10 mM NaPO$_4$, 60 mM NaCl pH 7.5. To the resulting solution was added 1/62.5 volume of 5M NaCl to yield final product.

While the present invention has been described in terms of a preferred embodiment, it is expected that modifications and improvements will occur to those skilled in the art upon consideration of this disclosure. Accordingly, it is intended that the appended claims cover all equivalents which come within the scope of the invention as claimed.

What is claimed is:

1. A process for isolating and purifying GM-CSF from a GM-CSF producing microorganism comprising:
   1) lysing the microorganism and separating insoluble material containing GM-CSF from soluble proteinaceous material;
   2) solubilizing the GM-CSF present in the insoluble material;
   3) oxidizing the GM-CSF in the presence of a reducing agent;
   4) selectively separating correctly folded GM-CSF from incorrectly folded GM-CSF by precipitating the incorrectly folded GM-CSF and retaining correctly folded GM-CSF in solution;
   5) recovering purified GM-CSF from the solution.

2. A process according to claim 1 wherein the GM-CSF in the insoluble material is solubilized using a chaotropic agent.

3. A process according to claim 2 wherein the GM-CSF is oxidized using oxidized glutathione in the presence of glutathione.

4. A process according to claim 3 wherein in step (4) the incorrectly folded GM-CSF is precipitated by adjusting the pH of the mixture to a range of 4.5–6.0.

5. A process according to claim 4 wherein the pH is adjusted to a range of 5.0 to 5.5.

6. A process according to claim 5 wherein the purified GM-CSF is recovered in step (5) by ion exchange chromatography or reverse phase high pressure liquid chromatography or combinations thereof.

7. A process for isolating and purifying GM-CSF from a GM-CSF producing microorganism comprising:
   1) lysing the microorganism and separating insoluble material containing GM-CSF from soluble proteinaceous material;
   2) solubilizing the GM-CSF present in the insoluble material;
   3) oxidizing the GM-CSF using oxidized glutathione in the presence of glutathione;
   4) adjusting the pH of the resulting mixture to a range of 4.5–6.0 to precipitate incorrectly folded GM-CSF and retain correctly folded GM-CSF in solution;
   5) recovering purified GM-CSF from the solution.

8. A process according to claim 7 wherein the GM-CSF in step (2) is solubilized using urea.

9. A process according to claim 8 wherein in step (4) the pH is adjusted using acetic acid.

10. A process according to claim 9 wherein step (2) is conducted at basic pH.

11. A process according to claim 10 wherein step (2) is conducted at a pH of 8.0–9.0 and at a urea concentration of from 6–8M.

12. A process according to claim 11 wherein in step (4) the pH is adjusted to a range of about 5.0. to 5.5.

13. A process according to claim 7 wherein the microorganism producing GM-CSF is *E. coli*.

* * * * *